(12) United States Patent  (10) Patent No.: US 9,301,728 B2
Yabugami  (45) Date of Patent: Apr. 5, 2016

(54) X-RAY APPARATUS

(75) Inventor: Katsuhiro Yabugami, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 382 days.

(21) Appl. No.: 13/700,050

(22) PCT Filed: Mar. 10, 2011

(86) PCT No.: PCT/JP2011/001409
§ 371 (c)(1),
(2), (4) Date: Nov. 26, 2012

(87) PCT Pub. No.: WO2011/148546
PCT Pub. Date: Dec. 1, 2011

(65) Prior Publication Data
US 2013/0077750 A1    Mar. 28, 2013

(30) Foreign Application Priority Data
May 26, 2010 (JP) ................................. 2010-120324

(51) Int. Cl.
*A61B 6/00* (2006.01)

(52) U.S. Cl.
CPC . *A61B 6/52* (2013.01); *A61B 6/481* (2013.01); *A61B 6/486* (2013.01); *A61B 6/504* (2013.01); *A61B 6/5235* (2013.01); *A61B 6/54* (2013.01); *A61B 6/488* (2013.01); *A61B 6/542* (2013.01)

(58) Field of Classification Search
CPC ....................................................... A61B 6/542
USPC .......................................................... 378/62
See application file for complete search history.

(56) References Cited

U.S. PATENT DOCUMENTS

| 5,347,563 | A | * | 9/1994 | Heidsieck | ........................ | 378/62 |
| 6,047,042 | A | * | 4/2000 | Khutoryansky et al. | ........ | 378/62 |
| 2002/0176535 | A1 | * | 11/2002 | Dixon et al. | ..................... | 378/62 |
| 2004/0101107 | A1 | | 5/2004 | Watanabe | | |
| 2006/0262904 | A1 | * | 11/2006 | Mertelmeier | .................... | 378/62 |

FOREIGN PATENT DOCUMENTS

| JP | 2003-209747 A | 7/2003 |
| JP | 2004-177251 A | 6/2004 |

* cited by examiner

*Primary Examiner* — Robert Kim
*Assistant Examiner* — Eliza Osenbaugh-Stewar
(74) *Attorney, Agent, or Firm* — McDermott Will & Emery LLP

(57) ABSTRACT

A mask-image-taking-time calculating section 36 (i) sets a first imaging-time, in a first mask image, in accordance with X-ray imaging-conditions, and (ii) calculates a second imaging-time, in mask images from the second, for a mask image to be taken next in accordance with the imaging-time and brightness of the mask image taken previously such that average brightness of the mask image taken previously and a mask image to be taken next is target brightness. A live-image-taking-time calculating section 38 calculates an imaging-time for a live image in accordance with an actual imaging-time for the mask image having X-rays applied thereto from an X-ray irradiating device in accordance with the first or second imaging-time. An image processor 6 calculates a subtraction image by difference between a reference mask image obtained through averaging two or more mask images taken in accordance with the first or second imaging-time and the live image.

9 Claims, 6 Drawing Sheets

X-RAY APPARATUS

RELATED APPLICATIONS

This application is the U.S. National Phase under 35 U.S.C. §371 of International Application No. PCT/JP2011/001409, filed on Mar. 10, 2011, which in turn claims the benefit of Japanese Application No. 2010-120324, filed on May 26, 2010, the disclosures of which Applications are incorporated by reference herein.

TECHNICAL FIELD

This invention relates to an X-ray apparatus that takes angiographic images. More particularly, this invention relates to an X-ray apparatus that sets an imaging time of a live image based on an imaging time of a mask image.

BACKGROUND

Conventionally, DSA (Digital Subtraction Angiography) has been conducted using an angiography contrast medium to obtain blood vessel images. DSA adopts an image processing technique that takes difference (subtraction) between image data prior to injecting the contrast medium (hereinafter, referred to as a mask image) and image data subsequent to injecting the contrast medium (hereinafter, referred to as a live image.) The difference between the mask image and the live image can cause elimination of an unnecessary portion for vascular diagnosis for bones or the like from the live image. Thereby a subtraction image containing an image of a blood vessel with the contrast medium injected thereinto needed for diagnosis can be obtained, and thus the blood vessel is readily visible. For conducting DSA satisfactorily, two or more mask images are obtained and they are averaged, whereby a reference mask image is generated. The reference mask image is subtracted from the live image to obtain a desired subtraction image.

When the mask image and the live image are taken with fixed values of tube voltage, tube current, and imaging time in such DSA, brightness of the fluoroscopic image often differs from target brightness depending on size or thickness of a subject. As a result, variation occurs in the brightness of the subtraction image depending on the subject.

However, change of a tube voltage during DSA causes different quality of X-rays. Thus, the tube voltage with a fixed value is desirable.
Moreover, a tube current value is controlled by filament current. Although the filament current is controlled, response to the tube current value in a short time is slow due to thermal inertia of a filament. Accordingly, a tube current value with a fixed value is also desirable. For the reasons as above, it is desirable that the brightness of the fluoroscopic image is controlled through control of the imaging time.

Then, an X-ray apparatus as described in Japanese Patent Publications No. 2003-209747A and 2004-177251 have been designed with AEC (automatic exposure control function.) The AEC has a function of monitoring a dose of X-ray irradiation by a phototimer and intercepting X-ray irradiation upon reaching a target dose. That is, control of the imaging time can achieve control of the dose of X-rays and the brightness of the taken image. In the DSA, it is desirable to take a mask image and a live image at the same brightness. Thus the imaging time is controlled in real time with the AEC upon taking the first mask image to detect an optimal imaging time. Then mask images and the live images from the second are imaged using the detected imaging time. Thus, the imaging time is controlled in real time with the AEC, thereby the imaging time can be obtained for which suitable brightness is achieved.

SUMMARY

The phototimer used upon adopting the AEC is attached on a subject side of a flat X-ray detector. Consequently, intensity of X-rays attenuates when X-rays pass through the phototimer. In addition, when the imaging time is controlled using image brightness information detected by the flat X-ray detector without using the phototimer, a delay of several tens ms to several hundreds ms occurs from applying X-rays up to reading out the image brightness information by the flat X-ray detector. In other words, such control cannot be made like the phototimer as immediately intercepting X-rays upon reaching target brightness through monitoring by the flat X-ray detector. As a result, it has been regarded as unsuitable to control the brightness of the taken image with no use of the phototimer.

This invention has been made regarding the state of the art noted above, and its object is to provide an X-ray apparatus that can obtain a subtraction image having appropriate brightness with no use of a phototimer.

This invention is constituted as stated below to achieve the above object. This invention includes an X-ray irradiating device; an X-ray detector; an imaging-condition setting section; a mask-image taking time calculating section; a live-image taking time calculating section; and an image processor. The X-ray irradiating device irradiates a subject with X-rays. The X-ray detector detects X-rays transmitting through the subject. The imaging-condition setting section sets X-ray imaging conditions for applying X-rays from the X-ray irradiating device. The mask-image taking time calculating section (i) sets a first imaging time, in a first mask image, in accordance with the X-ray imaging conditions, and (ii) calculates a second imaging time, in mask images from the second, for a mask image to be taken next in accordance with the imaging time and brightness of the mask image taken previously such that average brightness of the mask image taken previously and the mask image to be taken next is target brightness. The live-image taking time calculating section calculates an imaging time for a live image in accordance with the imaging time for the mask image to which X-rays are applied from the X-ray irradiating device in accordance with the first or the second imaging time. The image processor inputs detection signals detected by the X-ray detector and calculates a subtraction image by difference between a reference mask image and the live image, the reference mask image being obtained through averaging two or more mask images taken in accordance with the first or the second imaging time.

According to the aforementioned configuration, the X-ray irradiating device irradiates the subject with X-rays. The X-ray detector detects X-rays transmitting through the subject. The imaging-condition setting section sets X-ray imaging conditions for applying X-rays from the X-ray irradiating device. The mask-image taking time calculating section (i) sets a first imaging time, in a first mask image, in accordance with the X-ray imaging conditions, and (ii) calculates a second imaging time, in mask images from the second, for a mask image to be taken next in accordance with the imaging time and brightness of the mask image taken previously such that average brightness of the mask image taken previously and the mask image to be taken next is target brightness.

The live-image taking time calculating section calculates an imaging time for the live image in accordance with the imaging time for the mask image to which X-rays are applied from the X-ray irradiating device in accordance with the first or the second imaging time. The image processor inputs detection signals detected by the X-ray detector and calculates a subtraction image by difference between a reference mask image and the live image, the reference mask image being obtained through averaging two or more mask images taken in accordance with the first or the second imaging time.

The second imaging time as an imaging time for the mask images from the second is calculated such that the average brightness of the mask image taken previously and the mask image to be taken next is target brightness. Consequently, the brightness of the reference image can be the target brightness, the reference mask image being obtained through averaging two or more mask images taken in accordance with the first or the second imaging time. Moreover, the imaging time of the live image is calculated in accordance with the imaging time of the mask image to which X-rays are applied in accordance with the first or the second imaging time, also resulting in appropriate control of the brightness of the live image.

As a result, the reference mask image, the live image, and the subtraction image with suitable brightness can be obtained with no use of the phototimer. Needless of the phototimer can achieve reduction of costs. In addition, the DSA imaging system can be constructed with no failure due to operation failure of the phototimer. Moreover, since the phototimer is not needed to be adjusted, an installation time of the X-ray apparatus can be decreased. Furthermore, omit of the phototimer can avoid attenuation of X-rays by the phototimer, and can increase doses of incident X-rays to the X-ray detector, which achieves enhanced image quality.

Moreover, provided are an image-brightness storing section for storing the brightness of the mask image; an imaging-time measuring device for measuring an imaging time for which X-rays are actually applied from the X-ray irradiating device in accordance with the first or the second imaging time; and an imaging-time storing section for storing the actual imaging time of the mask image measured by the imaging-time measuring device. The mask-image taking time calculating section calculates the imaging time for a mask image to be taken next in the mask images from the second in accordance with the actual imaging time of the mask image taken previously that is stored in the imaging-time storing section and the brightness of the mask image taken previously that is stored in the image-brightness storing section. Such configuration is preferable.

According to the aforementioned configuration, the image-brightness storing section stores the brightness of the mask images. The imaging-time measuring device measures the imaging time for which X-rays are actually applied from the X-ray irradiating device in accordance with the first or the second imaging time. The imaging-time storing section stores an actual imaging time of the mask image measured by the imaging-time measuring device. The mask-image taking time calculating section calculates the imaging time for a mask image to be taken next in the mask images from the second in accordance with the actual imaging time of the mask image taken previously that is stored in the imaging-time storing section and the brightness of the mask image taken previously that is stored in the image-brightness storing section. Thereby, when a mask image is taken applying temporal restriction to the second imaging time, the brightness of the reference mask image can be brought close to the target brightness. That is because the second imaging time is calculated in accordance with the actual imaging time of the mask image previously taken.

Moreover, a brightness correcting section is provided for correcting the brightness of the mask image such that a ratio of the imaging time for the mask image corresponds linearly to a ratio of the brightness of the mask image. The mask-image taking time calculating section calculates the second imaging time using corrected brightness that is corrected by the brightness correcting section as the brightness. Such configuration is preferable.

According to the aforementioned configuration, the brightness correcting section corrects brightness of the mask image such that a ratio of the imaging time for the mask image corresponds linearly to a ratio of the brightness of the mask image. Consequently, although the ratio of the imaging time for the mask image does not correspond linearly to the brightness ratio of the mask image, the brightness in the mask image can be controlled through control of the imaging time for the mask image.

The mask-image taking time calculating section preferably calculates the second imaging time in accordance with the brightness and the imaging time of each mask image previously taken. Thereby influences from blurs partially generated in the mask image due to movement of the subject can be reduced.

The mask-image taking time calculating section may calculate the second imaging time in accordance with the brightness and the imaging time of the first mask image not in accordance with the brightness and the imaging time of the mask images from the second. Thus calculation of the second imaging time not in accordance with the brightness and the imaging time of the mask images from the second results in a reduced arithmetic load and rapid radiography of the mask image.

Moreover, an image average-brightness calculating section is preferably provided for calculating average brightness of a region of interest in the mask image as the brightness. Limitation to the region of interest in the mask image can achieve a reduced calculation amount for calculating the second imaging time and thus can achieve rapid process. In addition, calculation of the second imaging time using the average brightness of the region of interest can reduce influences of noises in the mask image. Moreover, the region of interest is preferably a central region of the mask image. Thereby a subtraction image can be generated that is easily interpreted by a radiographer.

Moreover, the live-image taking time calculating section may calculate an average value of the imaging time for each mask image as the imaging time of the live image. Thereby the brightness of the reference mask image may be identical to that of a portion of the live image to be eliminated through subtraction.

Moreover, the live-image taking time calculating section may calculate the imaging time of the live image through multiplying the ratio of the target brightness of the mask image and that of the live image to the average value of the imaging time for each mask image. Thereby, the live image with desired brightness relative to the brightness of the reference mask image can be obtained.

This invention can provide an X-ray apparatus that can obtain a subtraction image with appropriate brightness with no use of a phototimer.

DESCRIPTION OF REFERENCES

Figure 1:
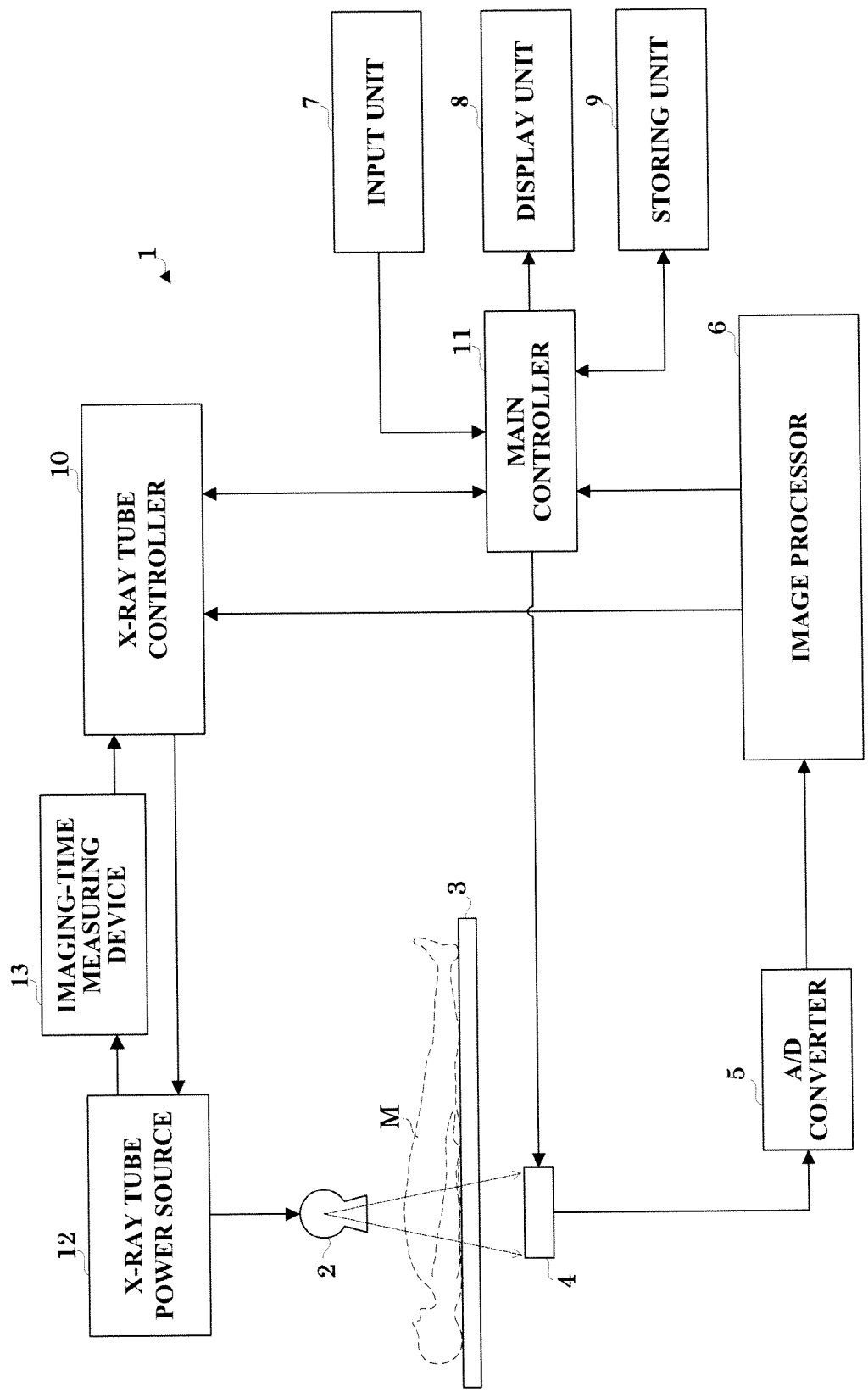
FIG. 1 is an overall view of an X-ray apparatus according to one example.

1 . . . X-ray apparatus
2 . . . X-ray tube
4 . . . FPD
6 . . . image processor
13 . . . imaging-time measuring device
30 . . . imaging-condition setting section
34 . . . average brightness calculating section
35 . . . image-brightness storing section
36 . . . mask-image taking time calculating section
37 . . . imaging-time storing section
38 . . . live-image taking time calculating section
42 . . . brightness correcting section

DETAILED DESCRIPTION

Example 1

1. X-ray Apparatus

Hereinafter, description will be given of examples of the present invention with reference to the drawings.

Figure 2:
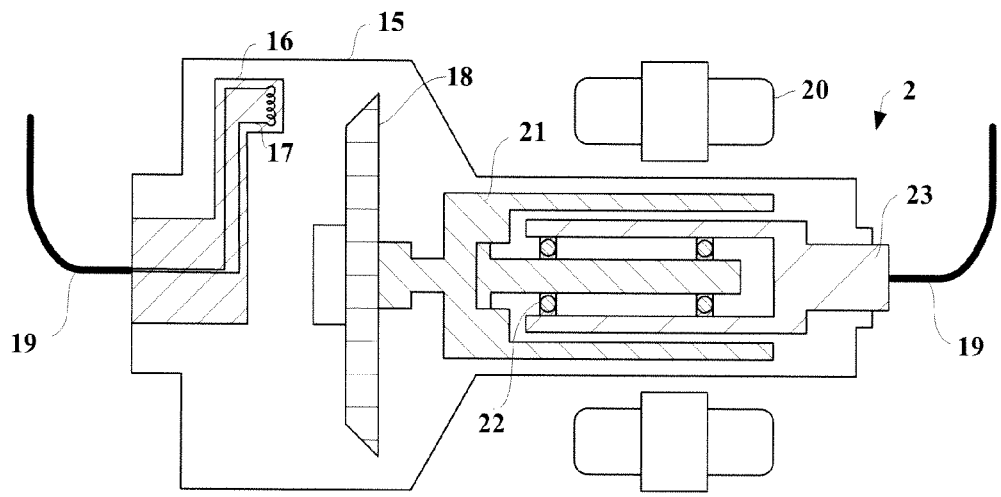
FIG. 2 is a schematic sectional view of an X-ray tube according to the example.
Figure 3:
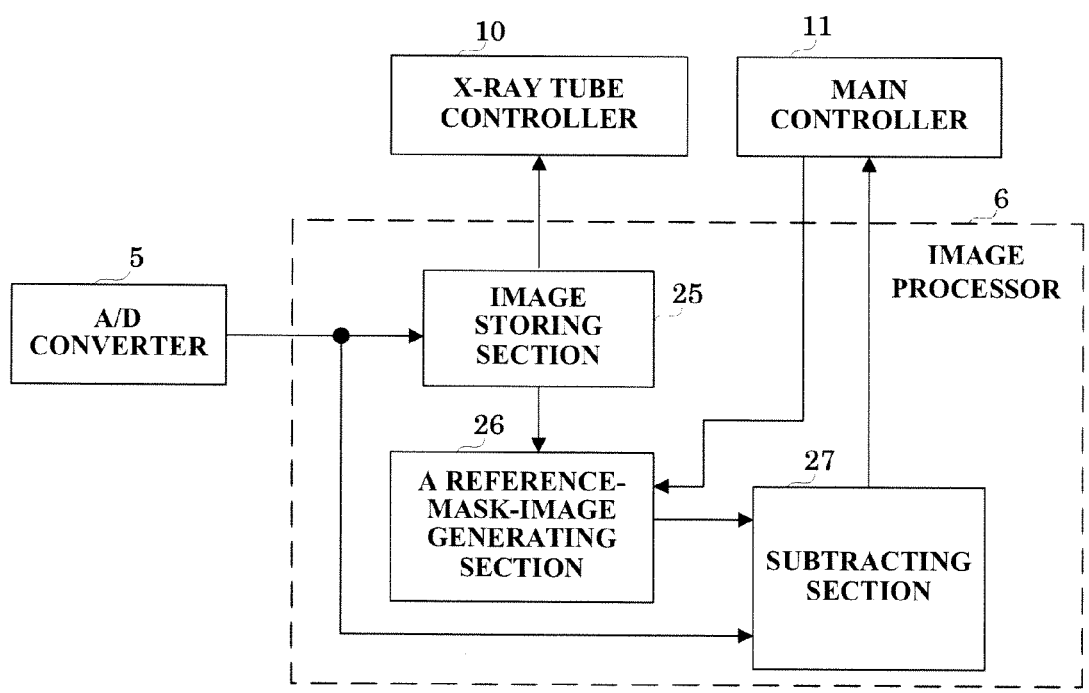
FIG. 3 is a block diagram showing an image processor according to the example.

FIG. 1 is an overall view of an X-ray apparatus. FIG. 2 is a schematic sectional view of an X-ray tube. FIG. 3 is a block diagram showing an image processor.

As shown in FIG. 1, the X-ray apparatus 1 includes an X-ray tube 2 for irradiating a subject M with X-rays; a top board 3 for supporting the subject placed thereon; a flat X-ray detector (a flat panel detector: hereinafter, referred to as an FPD) 4 for detecting X-rays transmitting through the subject M; and an A/D converter 5 for converting analog X-ray detection signals outputted from the FPD 4 into digital X-ray detection signals. Here, the X-ray tube 2 corresponds to the X-ray irradiating device in this invention, and the FPD 4 corresponds to the X-ray detector in this invention.

The X-ray apparatus 1 also includes an image processor 6 for performs various image processes through inputting digital X-ray detection signals; an input unit 7 for performing various input settings by a radiographer; a display unit 8 for displaying an operation screen for X-ray diagnosis and a fluoroscopic X-ray image subjected to image processing; a storing unit 9 for storing the fluoroscopic X-ray image and other radiography data; an X-ray tube controller 10 for controlling irradiation conditions of X-rays outputted to the X-ray tube 2 in accordance with instructions inputted into the input unit 7; and a main controller 11 for controlling en block these components.

The X-ray apparatus 1 further includes an X-ray tube power source 12 for supplying tube voltage and filament current to the X-ray tube 2 in accordance with the irradiation conditions of X-rays set by the X-ray tube controller 10; and an imaging-time measuring device 13 for measuring time for which pulse voltage is actually outputted from the X-ray tube power source 12 to the X-ray tube 2, i.e., an X-ray radiography time.

The FPD 4 has, for example, 2000×2000 X-ray detection pixels in a two-dimensional array for converting X-rays into charge signals. An X-ray detection pixel is composed of an X-ray detection element that generates charge signals upon X-ray irradiation. Thus, FPD 4 may be a direct-conversion type X-ray detector, or may be an indirect-conversion type X-ray detector.

The main controller 11 includes a central processing unit (CPU). The input unit 7 has a pointing device, typically a mouse, a keyboard, a joystick, a trackball, or a touch panel. A radiographer can set and input imaging conditions of the subject and radiography sites via the input unit 7. The display unit 8 includes a liquid crystal display, a CRT, or the like. The storing unit 9 includes a flash memory, a hard disk, a storage, or the like.

As shown in FIG. 2, examples of the X-ray tube 2 include a rotating anode X-ray tube. In the rotating anode X-ray tube, X-rays are generated through colliding electron beams emitted from a filament 17 placed inside a cathode 16 against a rotating anode 18 within an enclosure 15 with an inside thereof being vacuum. Filament current is supplied to the filament 17 from the X-ray tube power source 12 via a cable 19 to generate thermions in the filament 17. Under this state, high tube voltage is applied to the cathode 16 and the anode 18 from the X-ray tube power source 12 via the cable 19. Then the thermions generated in the cathode 16 collide against the anode 18 in a beam shape, whereby tube current is conducted.

The anode 18 is connected to a rotor 21 rotating due to rotation force from a stator 20. The rotor 21 is connected via a bearing 22 to a fixed portion 23, to which a lead 19 on an anode side is connected. Thus, high voltage is supplied from the lead 19 on the anode side via the fixed portion 23, the bearing 22, and the rotor 21 to the anode 18, whereas high voltage is supplied from the lead 19 on the cathode side to the cathode 16.

As shown in FIG. 3, the image processor 6 includes an image storing section 25 for storing X-ray detection signals inputted from the A/D converter 5 for every frame as a radiographic image; a reference mask-image generating section 26 for generating a reference mask image through averaging two or more radiographic images taken as the mask images; and a subtracting section 27 for subtracting the reference mask image from the live image inputted from the A/D converter 5. Image brightness information on each mask image stored in the image storing section 25 is sent to the X-ray tube controller 10. In the subtracting section 27, a subtraction image obtained through subtracting the reference mask image from the live image is sent to the main controller 11, and is displayed on the display unit 8 or is stored in the memory unit 9. The image processor 6 includes a microprocessor and a memory.

2. Luminance Control of Mask Image

Next, description will be given of the principle of controlling brightness in a mask frame according to one example. Here, let average brightness of the region of interest in a mask image be $X_n$. The region of interest is usually a center portion of a radiographic image. Let, for example, average brightness in the first mask image be $X_1$, and average brightness in the second mask image be $X_2$. That is, let average brightness in the Nth mask image be $X_N$.

For the first mask image, an imaging time $T_1$set is set in accordance with size and inspection site of the subject. The imaging time $T_1$set is expected that target brightness Xref may be obtained in accordance with imaging conditions of the subject. Moreover, the imaging time $T_1$set is an imaging time for which the brightness in the radiographic image does not fall to an over range or an under range. Here, the imaging time $T_1$set corresponds to the first imaging time in this invention.

After irradiation with X-rays in the first mask image, brightness signals of the first mask image are read out from the image processor 6 via the FPD 4 before irradiation with X-rays in the second mask image, whereby average brightness $X_1$ is calculated by the X-ray tube controller 10. Here, brightness control of the mask image in this example has a purpose to satisfy the equation below:

[Equation 1]

$$\sum_{n=1}^{N} \frac{X_n}{N} = Xref \quad (1)$$

That is, the purpose is to control brightness such that the average brightness of the mask image taken previously and the mask image to be taken next may be target brightness.

In order to achieve the purpose, a set value of the second imaging time $T_2$set is calculated such that the average brightness of the average brightness $X_1$ in the first mask image and the average brightness $X_2$ in the second mask image may be the target brightness Xref. Here, let the target brightness of the average brightness $X_2$ in the second mask image be $X_2$set, the equation below should be satisfied such that an average value of the average brightness $X_1$ in the first mask image and the average brightness $X_2$ in the second mask image may be the target brightness Xref.

[Equation 2]

$$Xref = \frac{X_1 + X_{2set}}{2} \quad (2)$$

Deformation of Equation (2) leads to the equation below.

[Equation 3]

$$X_{2set} = 2 \cdot Xref - X_1 \quad (3)$$

This example has an assumption that the brightness value is proportional to the imaging time. As a result, $T_1/X_1$ as a ratio of the actual first imaging time $T_1$ and the average brightness $X_1$ in the first mask image is calculated, whereby an imaging time per unit brightness value can be calculated. Then $X_2$set as the target brightness is multiplied to the ratio, whereby a set value of imaging time $T_2$set necessary for obtaining the target brightness $X_2$set can be calculated as the equation below:

[Equation 4]

$$T_{2set} = X_{2set} \cdot \frac{T_1}{X_1} \quad (4)$$

Equations (3) and (4) lead the equation below.

[Equation 5]

$$T_2 \text{ set} = (2 \cdot Xref - X_1) \cdot \frac{T_1}{X_1} \quad (5)$$

That is, the imaging time $T_2$set for irradiation in the second mask image is calculate in accordance with the average brightness $X_1$ and the actual imaging time $T_1$ in the first mask image, and the target brightness Xref such that the average brightness of the average brightness $X_1$ in the first mask image and the average brightness in the second mask image is the target brightness Xref. The brightness in the second mask image is controlled through adjusting the imaging time for the second mask image with respect to deviation between the average brightness $X_1$ in the first mask image and the target brightness Xref.

The actual imaging time, however, has restrictions such as restrictions in the shortest irradiation time and the longest irradiation time of the FPD 4 or an imaging system. Accordingly, the second mask image is taken while these restrictions are applied to the set value of imaging time $T_2$set to obtain the actual imaging time $T_2$ for the second mask image.

When the actual imaging time $T_2$ differs from the set value for imaging time $T_2$set, the average brightness $X_2$ in the second mask image taken for the actual imaging time $T_2$ differs from the target brightness $X_2$set of the average brightness $X_2$ in the second mask image. Thereby the average brightness of the average brightness $X_1$ in the first mask image and the average brightness $X_2$ in the second mask image differs from the target brightness Xref. Then, the set value for imaging time $T_3$set for the third mask image is calculated by the equation below.

[Equation 6]

$$T_3 \text{ set} = \{3 \cdot Xref - (X_1 + X_2)\} \cdot \frac{T_1 + T_2}{X_1 + X_2} \quad (6)$$

That is, an imaging time $T_3$set for the third mask image is calculated in accordance with the average brightness $X_1$, $X_2$ and the actual imaging time $T_1$, $T_2$, respectively, in the first and second mask images, and the target brightness Xref such that an average brightness of the average brightness $X_1$ in the first mask image, the average brightness $X_2$ in the second mask image, and the average brightness in the third mask image is the target brightness Xref.

Here, let $T_N$ be the actual imaging time for the Nth mask image. For instance, let $T_1$ be the actual imaging time for the first mask image, and $T_2$ be the actual imaging time for the second mask image. Then a set value $T_N$set for imaging time for the Nth is calculated by the equation below:

[Equation 7]

$$T_N \text{ set} = \frac{\left(N \cdot Xref - \sum_{n=1}^{N-1} X_n\right) \cdot \sum_{n=1}^{N-1} T_n}{\sum_{n=1}^{N-1} X_n} \quad (7)$$

As above, the imaging time of the mask image to be taken next from the second mask image is calculated in accordance with the imaging time and the brightness of the mask image previously taken such that the average brightness of the mask image previously taken and the mask image to be taken next is the target brightness. Thereby the average value of the brightness in each mask image $X_1, X_2, \ldots X_N$ can approach the target brightness Xref. As the number of the taken mask images increases, the average brightness of each mask image can approach the target brightness Xref.

3. X-ray Tube Controller

Figure 4:
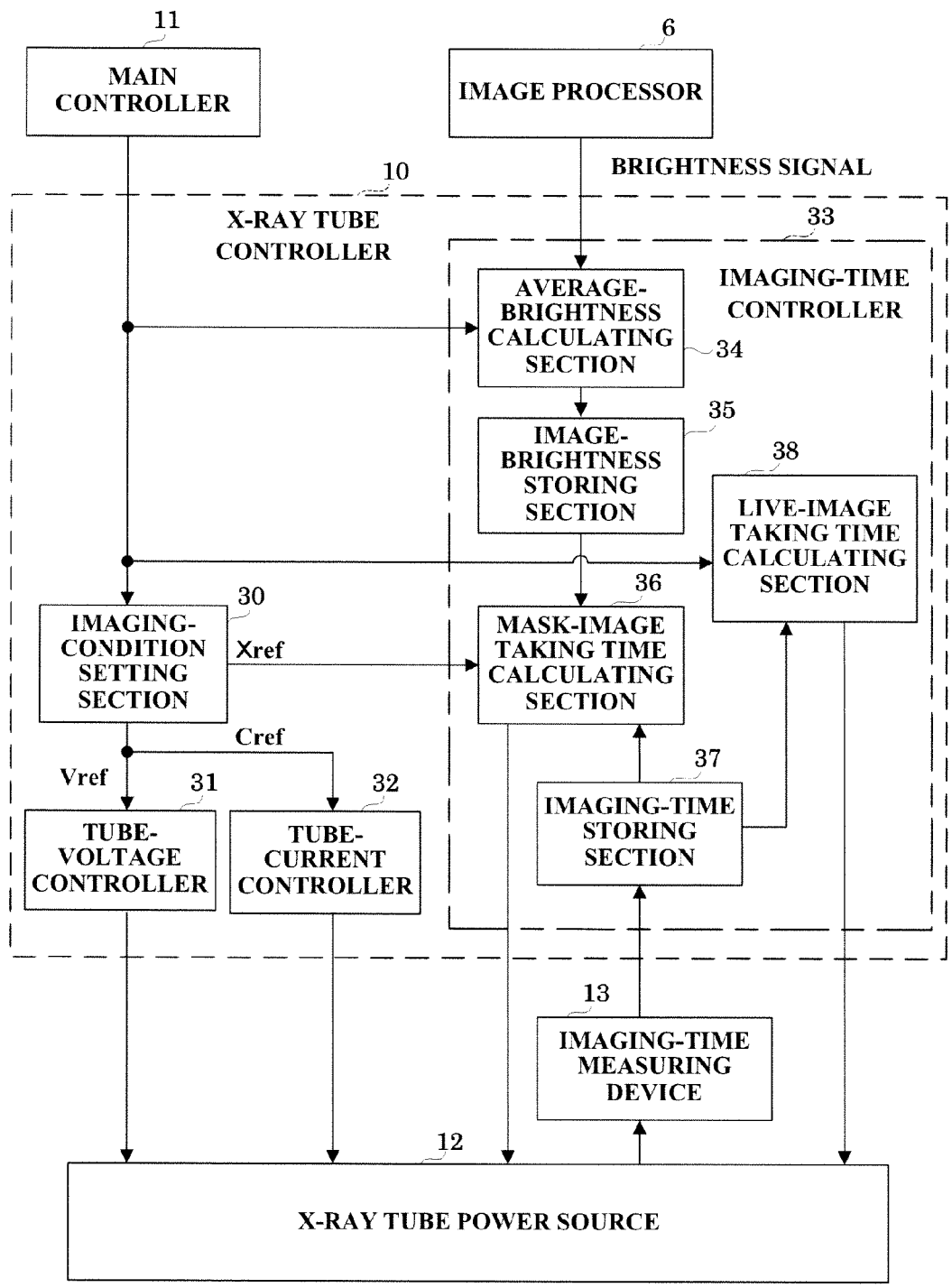
FIG. 4 is a block diagram showing an X-ray tube controller according to the example.

Description will be given of an X-ray tube controller that controls the brightness of the mask image mentioned above with reference to FIG. 4. FIG. 4 is a block diagram showing an X-ray tube controller.

An X-ray tune controller 10 includes an imaging-condition setting section 30 for setting X-ray imaging conditions in accordance with instructions from the main controller 11; a tube-voltage controller 31 for controlling a tube voltage value in accordance with instructions from the imaging-condition setting section 30; a tube-current controller 32 for controlling a tube current value in accordance with the instructions from the imaging-condition setting section 30; and an imaging-time controller 33 for controlling an imaging time in accordance with image brightness signals sent from an image processor. The X-ray tube controller 10 includes a microprocessor and a memory.

The imaging-condition setting section 30 sets X-ray imaging conditions with reference to a look-up table, such as the tube-voltage value Vref, the tube-current value Cref, and the target brightness Xref depending on size and inspection site of the subject, that are inputted into the input unit 7. The imaging-condition setting section 30 may set X-ray imaging conditions in accordance with information obtained through X-ray radiography prior to taking the mask image, such as a thickness of the subject.

The tube-voltage controller 31 controls the value of tube voltage that is applied to the X-ray tube 2. The tube-voltage controller 31 controls the pulse tube voltage outputted from the X-ray tube power source 12 in accordance with the tube voltage value Vref sent from the imaging-condition setting section 30.

The tube current controller 32 controls the value of the tube current that flows in the X-ray tube 2 through controlling the value of the filament current in the X-ray tube 2. The tube voltage controller 31 controls the filament current outputted from the X-ray tube power source 12 in accordance with the tube current value Cref sent from the imaging-condition setting section 30.

The imaging-time controller 33 sets the imaging time of the mask image and the live image, and controls an applying time of pulse tube voltage applied from the X-ray tube power source 12 to the X-ray tube 2, i.e., the imaging time. The imaging-time controller 33 includes an average-brightness calculating section 34 for calculating image average brightness of the taken image sent from the image processor 6; an image-brightness storing section 35 for storing the average image brightness; a mask-image taking time calculating section 36 for calculating the imaging time for the mask image; an imaging-time storing section 37 for storing the imaging time for the mask image measured by the imaging-time measuring device 13; and a live-image taking time calculating section 38 for calculating imaging time for the live image.

The average brightness calculating section 34 calculates the average brightness $X_1, X_2, \ldots X_N$ of the region of interest in each mask image. The region of interest is usually a central portion of the radiography image. Alternatively, the region of interest may be specified via the input unit 7 by a radiographer. The specified region of interest is instructed via the main controller 11 to the average brightness calculating section 34. The calculated average brightness $X_1, X_2, \ldots X_N$ in each mask image is sent to the image-brightness storing section 35.

The image-brightness storing section 35 stores the average brightness $X_1, X_2, \ldots X_N$ of the region of interest in each mask image calculated by the average brightness calculating section 34. The stored average image brightness in each mask image is sent to the mask-image taking time calculating section 36.

When a mask image to be taken next is the first, the mask-image taking time calculating section 36 sets imaging time $T_1$set in accordance with the target brightness Xref sent from the imaging-condition setting section 30. Moreover, when a mask image from the second is taken, the imaging time $T_N$set for the mask image to be taken next is calculated through Equation (7) in accordance with the target brightness Xref sent from the imaging-condition setting section 30, the average brightness in each taken mask image that is stored in the image-brightness storing section, and the actual imaging time for each taken mask image that is stored in the imaging-time storing section 37. The set imaging time $T_N$set is sent to the X-ray tube power source 12.

The imaging-time storing section 37 stores the actual imaging times $T_1, T_2, \ldots T_N$ in each mask image to which pulse tube voltage has been actually applied from the X-ray tube power source 12.

The live-image taking time calculating section 38 sets live-image taking time in accordance with the actual imaging times $T_1, T_2, \ldots T_N$ in each mask image stored in the imaging-time storing section 37. In this example, an average value $T_{Ave}$ of the actual imaging time $T_1, T_2, \ldots T_N$ in each mask image is calculated to be set as the live-image taking time.

4. X-ray Radiography

Subsequently, description will be given of operation where fluoroscopic X-ray radiography is conducted with this example.

Firstly, a radiographer inputs imaging conditions, such as size or site of the subject, into the input unit 7. The inputted imaging conditions are sent to the imaging-condition setting section 30 via the main controller 11. The number of mask images to be taken may also be set via the input unit 7. In this example, description is to be made taking as an example the case where four mask images are taken.

Subsequently, when an instruction for starting taking a mask image is given to the input unit 7, the imaging-condition setting section 30 sents the tube voltage value Vref to the tube-voltage controller 31, the tube current value Cref to the tube-current controller 32, and the target brightness Xref to the mask-image taking time calculating section 36, respectively, in accordance with the inputted imaging conditions. The tube-voltage controller 31 gives instructs to the X-ray tube power source 12 so as to output the tube voltage value Vref to the X-ray tube power source 12. The tube current controller 32 instructs the filament current value to the X-ray tube 12 such that the tube current value Cref is generated in the X-ray tube 2.

Figure 5:
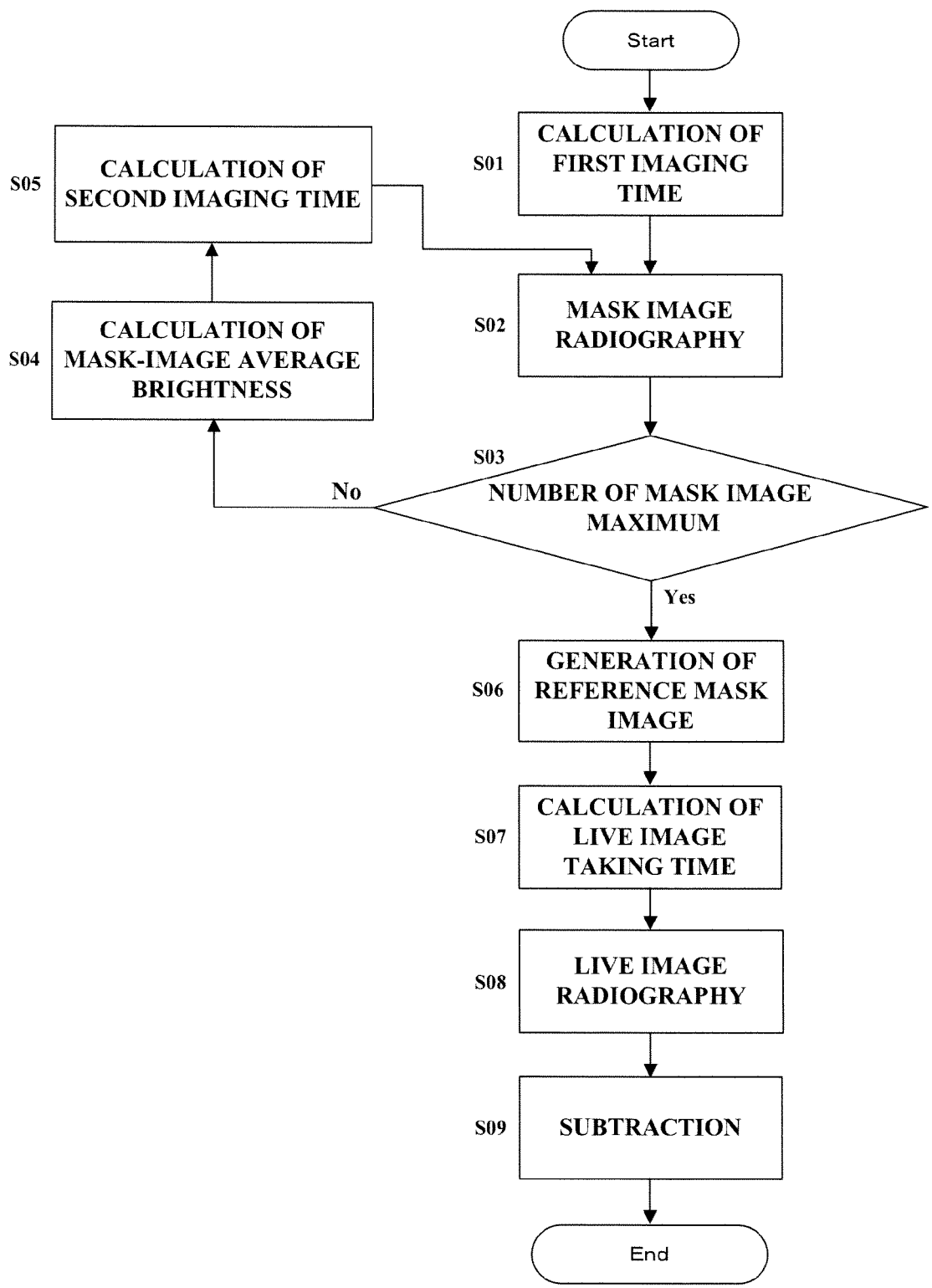
FIG. 5 is a flow chart showing a flow of generating a subtraction image according to the example.
Figure 6:
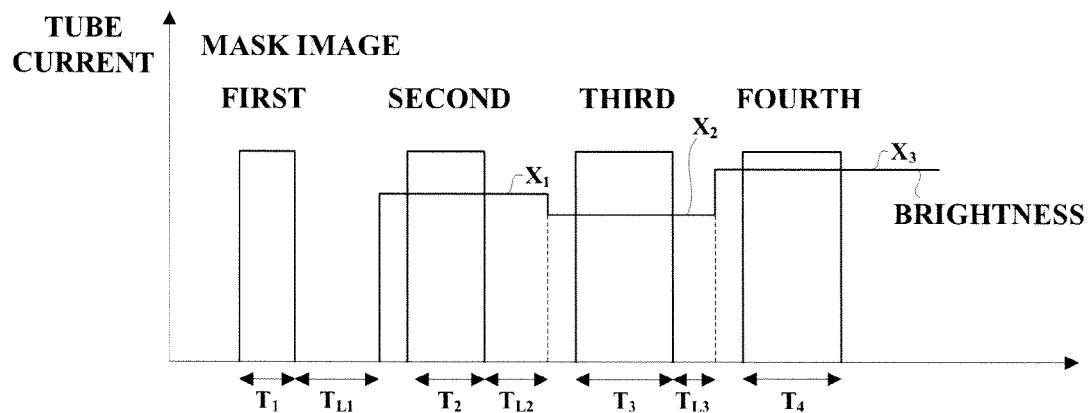
FIG. 6 is a timing chart of X-ray generation for a mask image.
Figure 7:
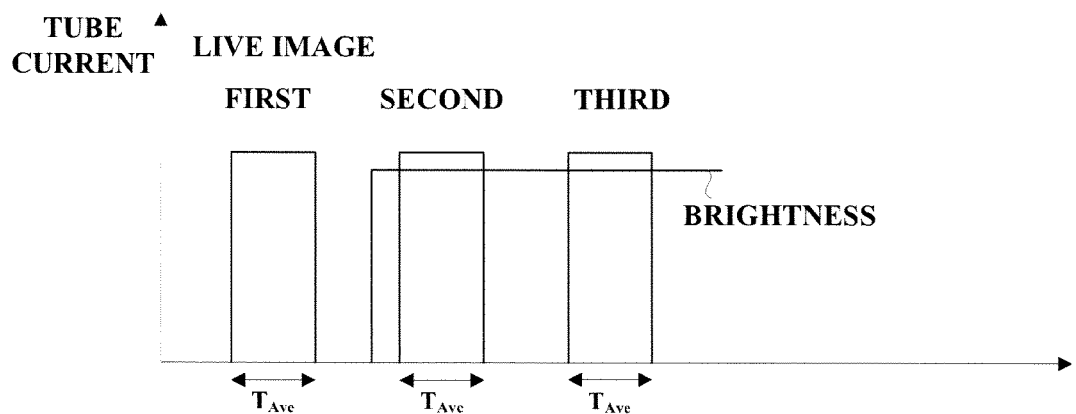
FIG. 7 is a timing chart of X-ray generation for a live image.

Subsequently, description will be given in order of generating a subtraction image with reference to FIGS. 5 through 7. FIG. 5 is a flow chart showing a flow of generating a subtraction image. FIG. 6 is a timing chart of X-ray generation in a mask image. FIG. 7 is a timing chart of X-ray generation in a live image.

Step S01 (Calculation of First Imaging Time)

The mask-image taking time calculating section 36 sets imaging time $T_1$set corresponding to the target brightness Xref with reference to a look-up table. The imaging time $T_1$set for the first mask image is determined in advance in the look-up table with respect to the target brightness Xref. The set imaging time $T_1$set is sent to the X-ray tube power source 12.

Step S02 (Mask Image Radiography)

The X-ray tube power source 12 outputs pulse voltage to the X-ray tube 2 in accordance with the X-ray tube voltage value, the filament current value, and the imaging time $T_1$ set sent from the X-ray tube controller 10, whereby X-rays are applied from the X-ray tube 2. Here, the time $T_1$ for which X-rays are actually applied is measured by the imaging-time measuring device 13. The measured actual imaging time T1 is sent to the imaging-time storing section 37, where it is stored. The first taken mask image is stored in the image storing section 25 in the image processor 6. The X-ray tube controller 10 sends to the main controller 11 a signal that the mask image has been taken. The main controller 11 counts the number of taken mask images.

Step S03 (Discrimination of Number of Taken Images)

Subsequently, the main controller 11 discriminates whether or not the number of taken mask images is the maximum. In this example, the number of taken mask images is set as four. Consequently, when the number of taken mask images is less than four, the process proceeds to Step S04. In this stage, since the number of taken mask images is one, the process proceeds to Step S04.

Step S04 (Calculation of Mask-image Average Luminance)

Subsequently, the brightness signals of the first mask image are sent from the image processor 6 to the average brightness calculating section 34 in the imaging-time controller 33, and the average brightness $X_1$ of the region of interest in the first mask image is calculated. The calculated average brightness $X_1$ is stored in the image-brightness storing section 35. A time lag $T_{L1}$ occurs from taking the first mask image until sending the brightness signals via the image processor 6 to the average brightness calculating section 34 and calculating the average brightness $X_1$.

Step S05 (Calculation of Mask-image Taking Time)

Subsequently, the mask-image taking time calculating section 36 reads the actual imaging time $T_1$ stored in the imaging-time storing section 37. The mask-image taking time calculating section 36 also reads the average brightness $X_1$ stored in the image-brightness storing section 35. Then the mask-image taking time calculating section 36 calculates the imaging time $T_1$set for the second mask image through Equation (5) in accordance with the average brightness $X_1$ and the actual imaging time $T_1$ of the first mask image.

Step S02 (Mask Image Radiography)

Here, a X-ray tube-voltage value and a filament current value are under the same condition of that upon taking the first mask image, and the imaging time is modified into $T_2$set. The X-ray tube power source 12 applies pulsed X-rays from the X-ray tube 2, and the second mask image is taken. Here, time $T_2$ for the second mask image for which X-rays are actually applied is measured by the imaging-time measuring device 13. The measured actual imaging time $T_2$ is sent to the imaging-time storing section 37, where it is stored. The taken second mask image is stored in the image storing section 25 in the image processor 6. The X-ray tube controller 10 sends a signal to the main controller 11 that the mask image has been taken. The main controller 11 counts the number of taken mask images.

Step S03 (Discrimination of Number of Taken Images)

Subsequently, the main controller 11 discriminates whether or not the number of taken mask images is the maximum. In this stage, since the number of taken mask images is two, the process proceeds to Step S04.

Step S04 (Calculation of Mask-image Average Luminance)

Subsequently, the brightness signals of the second mask image are sent from the image processor 6 to the average brightness calculating section 34 in the imaging-time controller 33, and the average brightness $X_2$ of the region of interest in the second mask image is calculated. The calculated average brightness $X_2$ is stored in the image-brightness storing section 35. A time lag $T_{L2}$ occurs from taking the second mask image until sending the brightness signals via the image processor 6 to the average brightness calculating section 34 and calculating the average brightness $X_2$.

Step S05 (Calculation of Second Imaging Time)

Subsequently, the mask-image taking time calculating section 36 reads the actual imaging time $T_1$, $T_2$ stored in the imaging-time storing section 37. The mask-image taking time calculating section 36 also reads the average brightness $X_1$, $X_2$ stored in the image-brightness storing section 35. Then the mask-image taking time calculating section 36 calculates the imaging time $T_3$set for the third mask image through Equation (6) in accordance with the average brightness $X_1$, $X_2$ and the actual imaging times $T_1$, $T_2$ of the first and second mask images.

Step S02 (Mask Image Radiography)

Here, a X-ray tube-voltage value and a filament current value are under the same condition of those upon taking the first and second mask images, and the imaging time is modified into $T_3$set. The X-ray tube power source 12 applies pulsed X-rays from the X-ray tube 2, and the third mask image is taken. Here, an imaging time $T_3$ of the third frame for which X-rays are actually applied is measured by the imaging-time measuring device 13. The measured actual imaging time $T_3$ is sent to the imaging-time storing section 37, where it is stored. The taken mask image is stored in the image storing section 25 in the image processor 6. The X-ray tube controller 10 sends a signal to the main controller 11 that the mask image has been taken. The main controller 11 counts the number of taken mask images.

Subsequently, Step S03, Step S04, Step S05, and Step S02 are repeated to take the fourth mask image. A time lag $T_{L3}$ occurs from taking the third mask image until sending the brightness signals via the image processor 6 to the average brightness calculating section 34 and calculating average brightness $X_3$. Then an imaging time $T_4$set for the fourth mask image is calculated through Equation (7) in accordance with the average brightness $X_1$, $X_2$, $X_3$ and the actual imaging times $T_1$, $T_2$, $T_3$ of all the taken mask images.

Step S03 (Discrimination of Number of Taken Images)

The number of taken mask images is four as the maximum. Subsequently, radiography of the mask images is completed, and the process proceeds to Step S06. The main controller 11 discriminates that the number of taken mask images has been the maximum, and gives instructions of generating a reference mask image to a reference mask image generating section 26.

Step S06 (Calculation of Reference Mask Image)

In the image processor 6, each mask image stored in the image storing section 25 is read into the reference mask image generating section 26. The reference mask image generating section 26 calculates a reference mask image as an average image of each mask image, and outputs it into a subtracting section 27. The average brightness of the region of interest in the reference mask image is the target brightness Xref.

Step S07 (Calculation of Live Image Taking Time)

Subsequently, a live-image imaging time calculating section 38 reads the actual imaging times $T_1$, $T_2$, $T_3$, and $T_4$ for each mask image stored in the imaging-time storing section to calculate a live image taking time in accordance with these values. In this example, the average value $T_{Ave}$ of the actual imaging times $T_1$, $T_2$, $T_3$, and $T_4$ is calculated to be a live image taking time. The calculated live image taking time is sent to the X-ray tube power source 12.

Step S08 (Live Image Radiography)

Subsequently, the X-ray tube power source 12 applies X-rays from the X-ray tube 2 to obtain a live image with imaging time as the live-image taking time and with the same condition of the X-ray tube voltage and the X-ray tube current in the mask-image taking. The live image has an area where a contrast medium has been imaged that is darker than an area corresponding to that of the mask image, and a portion in the taken live image to be removed, i.e., a background portion in the live image where the contrast medium has not been imaged, has the average brightness corresponding to the target brightness Xref.

Step S09 (Subtraction Generation)

The taken live image is subtracted with the reference mask image by the subtracting section 27 in the image processor 6, whereby a subtraction image is generated. Since the portions to be removed through subtraction in the reference mask image and the live image have the same average brightness, the generated subtract image has appropriate brightness that does not vary depending to the subject.

The subtraction image generated by the subtracting section 27 is displayed on the display unit 8 or stored in the storing unit 9 via the main controller 11.

As above, according to the X-ray apparatus 1 in this example, the second imaging time as an imaging time for the mask images from the second is calculated such that the average brightness of the mask image taken previously and the mask image to be taken next may be target brightness. Consequently, brightness of the reference mask image obtained through averaging a plurality of mask images taken in accordance with the first and second imaging times can be the target brightness. Moreover, the imaging time for the live image is calculated in accordance with the actual imaging time of the mask image to which X-rays are applied in accordance with the first and second imaging times. Consequently, the brightness of the live image can be controlled appropriately.

In other words, a time lag occurs in reading out brightness signals from the image processor 6. Consequently, although the average brightness $X_1, X_2, X_3, \ldots$ in the region of interest in each mask image does not reach the target brightness Xref, the average brightness in the region of interest in the reference mask image as the average image of each mask image can reach the target brightness Xref. Consequently, when a time lag occurs in reading out the brightness signals from the image processor 6, the suitable brightness in the reference mask image and the live image can be obtained.

As a result, the mask image and the live image having suitable brightness can be obtained with no use of the phototimer. Needless of the phototimer can achieve reduced costs and construction of the DSA imaging system with no failure due to operation failure of the phototimer. Moreover, since the phototimer is not needed to be adjusted, an installation time of the X-ray apparatus 1 can be decreased. Furthermore, omit of the phototimer can avoid attenuation of X-rays by the phototimer, and can increase doses of incident X-rays into the FPD 4, which achieves enhanced image quality.

Moreover, when a mask image is taken applying temporal restrictions to the second imaging time, the brightness of the reference mask image can be brought close to the target brightness. That is because the second imaging time is calculated in accordance with the actual imaging time for the mask image previously taken. Moreover, since the imaging time for each mask image is calculated individually, influences from blurs due to movement of the subject while taking each mask image can be reduced.

Limitation of calculating the average brightness of the mask image to the region of interest in the mask image can achieve a reduced calculation amount of calculating the second imaging time and process at high speed. In addition, calculation of the second imaging time using the average brightness of the region of interest can reduce influences of noises in the mask image. Moreover, setting the region of interest to a central region of the mask image can achieve generation of a subtraction image that is easily interpreted by a radiographer.

Example 2

Next, description will be given of another example in this invention. Example 2 has a variation of calculating the second imaging time in the mask image by the mask-image taking time calculating section in Example 1. Therefore, the fluoroscopic X-ray apparatus has the same configuration as that of Example 1 except for the configuration described hereinunder.

In Example 1, the second imaging time is calculated for each mask image in accordance with the brightness signals and the actual imaging time of each mask image. In Example 2, the same imaging time for the mask images from the second is calculated in accordance with the brightness signals and the actual imaging time of the first mask image.

Since imaging of the first mask image in Example 2 is similar to that in Example 1, the description thereof is to be omitted. A set value of imaging time $T_2$set from the second is measured by the equation below. The subsequent mask images are taken for the imaging time $T_2$set.

[Equation 8]

$$T_2 \text{ set} = \left(\frac{N \cdot Xref - X_1}{N - 1}\right) \cdot \frac{T_1}{X_1} \quad (8)$$

According to Example 2, the second imaging time is calculated in accordance with imaging results of the first mask image not with those of the mask images from the second, whereby the mask image can be taken with reduced calculation load and higher speed. As noted above, measuring only the average brightness $X_1$ and the actual imaging time $T_1$ of the region of interest in the first mask image can calculate the second imaging time for the mask images from the second. Consequently, for imaging the mask images from the second, the next mask image can be taken prior to reaching the brightness signals of the mask image from the image processor 6 to the X-ray tube controller 10. As a result, the next mask image can be taken before the brightness signals of the prior mask image reach. Thus the mask image can be taken at higher speed.

Example 3

Description will be given next of Example 3 in this invention. Example 3 includes a modification of the imaging time controller 33 in Examples 1 and 2. Accordingly, the X-ray apparatus has the same configuration as Example 1 except for the configuration described hereinunder. An imaging-time controller 41 in Example 3 has a configuration of adding a brightness correcting unit 42 to the imaging time controllers 33 in Examples 1 and 2. Thereby, the X-ray apparatus 1 is applicable to the case where the image brightness is not linearly outputted with respect to the imaging time.

Figure 8:
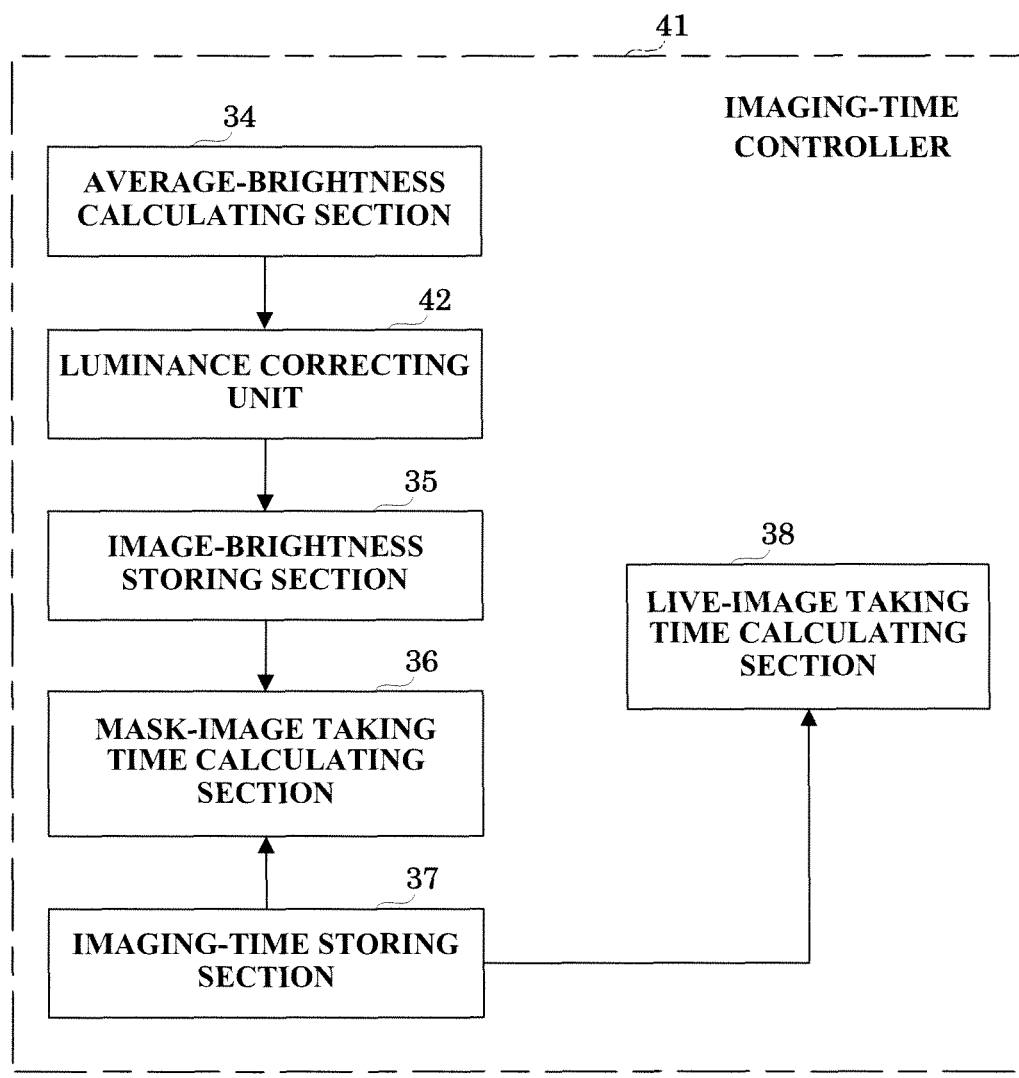
FIG. 8 is a block diagram showing an imaging time controller according to another example.

Reference is made to FIG. 8. FIG. 8 is a block diagram showing an imaging time controller according to Example 3. A brightness correcting unit 42 converts average brightness of a target region in a mask image calculated in the average brightness calculating section 34 into linear brightness with respect to an imaging time with reference to a look-up table. Thereby a ratio of the imaging time for the mask image corresponds to a ratio of the brightness in the mask image linearly. Accordingly, the mask-image taking time calculating section 36 calculates a second imaging time in accordance with the brightness corrected by the brightness correcting unit. Consequently, although the X-ray apparatus 1 does not output the image brightness linearly relative to the imaging time, control of the imaging time can achieve appropriate brightness in the reference mask image and the live image.

This invention is not limited to the foregoing embodiment, but may be modified as follows:

(1) In the foregoing examples, the imaging time for the live image is controlled such that the portions to be removed have the same brightness through subtraction with the average brightness in each mask image. Alternatively, the imaging time for the live image can be set such that the portions to be removed have brightness different from the average brightness in each mask image. In this case, the live-image taking time setting section 38 may multiply the brightness ratio of the mask image and the live image to the average value $T_{Ave}$ of the actual imaging time for the mask image.

For instance, let the target brightness of the mask image Xref be 100 and the target brightness where no contrast medium for the live image is injected be 120. A target ratio A of the mask image and the live image should be 1.2. Here, letting the imaging time for the live image be $A \cdot T_{Ave}$, the live image can obtain the brightness of 1.2 times of the target brightness Xref in the mask image.

(2) In the foregoing examples, the second imaging time is calculated in accordance with the actual imaging time of the mask previously taken. Alternatively, when no temporal restriction is given, the second imaging time can be calculated in accordance with imaging time $T_N$ set previously taken.

(3) In the foregoing examples, four mask images are taken for generating the reference mask image. This is, however, not limitative. At least two or more mask images may be taken.

(4) In the foregoing examples, the second imaging time is calculated after the brightness signals from the image processor 6 reach the X-ray tube controller 10. When the brightness signals from the image processor 6 delay by one or more frames after X-ray irradiation, i.e., when the first brightness signals are outputted after radiography of the second image, the second imaging time is not calculated until the brightness signals are outputted but is calculated after the brightness signals are outputted from the image processor to obtain the appropriate average brightness. Such control is preferable.

The invention claimed is:

1. An X-ray apparatus configured to obtain a reference mask image of a subject and a live image of the subject which includes information to be examined and is different from the reference mask image, and extract the information from the live image based on the reference mask image, the X-ray apparatus comprising:
    an X-ray irradiating device for irradiating a subject with X-rays;
    an X-ray detector for detecting X-rays transmitting through the subject;
    an imaging-condition setting section for setting X-ray imaging conditions for the X-ray irradiating device to irradiate the subject with the X-rays;
    a mask-image taking time calculating section for
        (i) setting a first imaging time for obtaining a first mask image of the subject, in accordance with the X-ray imaging conditions, and
        (ii) calculating a second imaging time for obtaining a mask image of the subject to be taken subsequent to the first mask image in accordance with imaging time and brightness of a mask image taken previously such that average brightness of the mask image taken previously and a mask image to be taken next is target brightness;
    a live-image taking time calculating section for calculating an imaging time for the live image in accordance with an imaging time of the mask image to which X-rays are emitted from the X-ray irradiating device based on the first imaging time and an imaging time of the mask image to which X-rays are emitted from the X-ray irradiating device based on the second imaging time; and
    an image processor for receiving detection signals of the X-rays detected by the X-ray detector and calculating a subtraction image based on a difference between the reference mask image and the live image, the reference mask image being obtained through averaging the mask image taken in accordance with the first imaging time and the mask image taken in accordance with the second imaging time.

2. The X-ray apparatus according to claim 1, further comprising:
    an image-brightness storing section for storing the brightness of the mask image;
    an imaging-time measuring device for measuring an imaging time for which X-rays are actually applied from the X-ray irradiating device in accordance with the first or the second imaging time; and
    an imaging-time storing section for storing the actual imaging time of the mask image measured by the imaging-time measuring device, wherein
    the mask-image taking time calculating section calculates the second imaging time in accordance with the actual imaging time of the mask image taken previously that is stored in the imaging-time storing section and the brightness of the mask image taken previously that is stored in the image-brightness storing section.

3. The X-ray apparatus according to claim 1, further comprising:
    a brightness correcting section for correcting the brightness of the mask image such that a ratio of the imaging time for the mask image corresponds linearly to a ratio of the brightness of the mask image, wherein
    the mask-image taking time calculating section calculates the second imaging time using corrected brightness that is corrected by the brightness correcting section as the brightness.

4. The X-ray apparatus according to claim 1, wherein the mask-image taking time calculating section calculates the second imaging time in accordance with the brightness and the imaging time of each mask image previously taken.

5. The X-ray apparatus according to claim 1, wherein the mask-image taking time calculating section calculates the second imaging time in accordance with the brightness and the imaging time of the first mask image not in accordance with the brightness and the imaging time of mask images of the subject to be taken subsequent to the first mask image.

6. The X-ray apparatus according to claim 1, further comprising: an image average-brightness calculating section for calculating average brightness of a region of interest in the mask image as the brightness.

7. The X-ray apparatus according to claim 6, wherein the region of interest is a central region of the mask image.

8. The X-ray apparatus according to claim 1, wherein the live-image taking time calculating section calculates an average value of the imaging time for each mask image as the imaging time of the live image.

9. The X-ray apparatus according to claim 1, wherein the live-image taking time calculating section calculates the imaging time of the live image through multiplying the ratio of the target brightness of the mask image and that of the live image to the average value of the imaging time for each mask image.

* * * * *